United States Patent
Cartwright et al.

(10) Patent No.: US 8,798,284 B2
(45) Date of Patent: Aug. 5, 2014

(54) USER SELECTABLE MASKING SOUNDS FOR MEDICAL INSTRUMENTS

(75) Inventors: Jason Cartwright, Libertyville, IL (US); David Howard, Gulfport, FL (US); Robert Childers, Trinity, FL (US); John Niedospial, Trinity, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1174 days.

(21) Appl. No.: 11/695,155

(22) Filed: Apr. 2, 2007

(65) Prior Publication Data

US 2008/0243211 A1 Oct. 2, 2008

(51) Int. Cl.
*H04R 3/02* (2006.01)
*G10K 11/175* (2006.01)

(52) U.S. Cl.
CPC .................................... *G10K 11/175* (2013.01)
USPC ........................................................ 381/73.1

(58) Field of Classification Search
CPC ......... G10K 7/04; G10K 7/06; G10K 15/043; G10K 5/00; G10K 7/00; G10K 11/16; G10K 11/175
USPC ............ 381/73.1, 71.1–71.14, 94.1–94.7, 77, 381/104, 57, 80, 82; 607/63; 128/845; 600/559, 300, 410; 324/307, 309, 318, 324/322
See application file for complete search history.

(56) References Cited

U.S. PATENT DOCUMENTS 5,427,102 A * 6/1995 Shimode et al. ............. 600/410
5,570,426 A * 10/1996 Gardner ....................... 381/71.6
6,047,074 A 4/2000 Zoels et al.
6,179,792 B1 * 1/2001 Krause .............................. 601/2
6,463,316 B1 10/2002 Brungart (Continued)

FOREIGN PATENT DOCUMENTS

JP 3-93251 9/1991
JP 6-87867 11/1991

(Continued)

OTHER PUBLICATIONS

A Low-Power Two-Digit Multi-dimensional Logarithmic Number System Filterbank Architecture for a Digital Hearing Aid; EURASIP Journal on Applied Signal Processing 2005:18, 3015-3025 © 2005 Hindawi Publishing Corporation; Roberto Muscedere, Vassil Dimitrov, Graham Jullien, William Miller.

(Continued)

*Primary Examiner* — Lun-See Lao
(74) *Attorney, Agent, or Firm* — K&L Gates LLP (57) ABSTRACT

A medical instrument includes a sound card or an internal capability for generating sounds from a digital music or sound file. The medical instrument is one which generates unwanted noise and is constantly in the presence of a patient or an operator, and may be in a home, a clinic, a laboratory, or other intimate setting. For instance, a patient may be typically connected for hours to a hemodialysis machine that has a noisy pump. A blood-plasma volunteer may be hooked to a noisy blood separation machine for a period of time. A laboratory technician may work in close proximity to a sample preparation machine that constantly gurgles and whirrs. In each instance, a sound card and a speaker can generate previously-recorded masking noises that make that the presence and operation of the machine more tolerable.

28 Claims, 9 Drawing Sheets

(56) References Cited

U.S. PATENT DOCUMENTS

| | | | |
|---|---|---|---|
| 7,460,675 B2 * | 12/2008 | L'Esperance et al. | 381/73.1 |
| 7,471,797 B2 * | 12/2008 | Moeller et al. | 381/73.1 |
| 8,477,958 B2 * | 7/2013 | Moeller et al. | 381/73.1 |
| 2003/0010345 A1 * | 1/2003 | Koblasz et al. | 128/845 |
| 2003/0144847 A1 * | 7/2003 | Roy et al. | 704/278 |
| 2003/0212328 A1 | 11/2003 | Bechtold et al. | |
| 2007/0104334 A1 * | 5/2007 | Dallam et al. | 381/77 |

FOREIGN PATENT DOCUMENTS

| | | |
|---|---|---|
| JP | 6-56388 | 8/1994 |
| JP | 11-155873 | 6/1999 |
| JP | 2002-318585 | 10/2002 |
| JP | 2003-310569 | 11/2003 |

OTHER PUBLICATIONS

Accelerated Slope Tone Control Equalizers, J. Audio Eng. Soc. vol. 40, No. 12, Dec. 1992, Dennis A. Bohn; Engineering Report.

Sound Control for Fenestration Products; AAMA TIR-A1-03; revised Nov. 2003, print date Dec. 2003; pp. 1-43.

Japanese Office Action mailed Jan. 4, 2013, corresponding to Japanese Application No. 2010-502187.

Japanese Office Action mailed Sep. 5, 2013, corresponding to Japanese Application No. 2010-502187.

* cited by examiner

USER SELECTABLE MASKING SOUNDS FOR
MEDICAL INSTRUMENTS

BACKGROUND

The field is that of medical instruments, including instruments for direct patient care at home, for laboratory use, and for clinical or hospital use in conjunction with patient care.

Patients and operators of medical machines and instruments may be under a good deal of stress, caused by health concerns and the need for using the medical instruments. These may include dialysis machines, blood separators, sample preparation machines, drug dose preparation devices, and so forth. The stress may be exacerbated by the need for close proximity to the machine for hours on end, such as an overnight peritoneal dialysis procedure. The constant noise made by such machines may be very aggravating and annoying to patients who must remain connected to the machine for hours on end. Other medical instruments that reside in close quarters with operating personnel, such as laboratory sample preparation machines with centrifuges, may also emit annoying sounds.

One way to avoid these sounds is to enclose the medical device or instrument in a separate room or enclosure. This will isolate the annoying sounds from the patient or user. However, some machines, such as blood separators or dialysis machines are better used with short runs of tubing to the patient, and separate enclosures may not be practical. Another way is to provide a separate sound system to generate masking sounds or to play music. This method, however, would require a separate sound system for each medical device, and would be both expensive and cumbersome.

Some medical instruments have artifacts by which they generate their own "masking sounds." For example, a compressor that operates a dialysis system generates a constant hum that masks other sounds from the instrument, such as the venting of air or the clicking of valves. While the hum itself is not annoying, the hum will change pitch depending on its load and also depending on the portion of the dialysis cycle. This change in pitch, sometimes also accompanied by a change in volume, is noticeable to the patient. Other techniques in general use include efforts to reduce overall machine noise. When a particular noise is eliminated, however, other noises may then become apparent. An example is using a housing or baffles to enclose and silence the above-mentioned compressor. Once the compressor is silenced, the clicking of the valves, the creaking of the dialysis door assembly, and even the swishing of fluid within the dialysis disposable portion become relatively louder and more noticeable.

What is needed is a way to reduce or mask noise of medical instruments so that the instrument is less noticeable to a user or an operator of the instrument. The method used should not interfere with operation of the machine, should be economical, and not require any further separation of the medical instrument from the patient or user. It would also be desirable if the method could be retrofitted onto existing medical instruments.

SUMMARY

One embodiment is a medical instrument. The embodiment includes a medical instrument for patient care, laboratory use, or pharmaceutical use, a computer, the computer forming a part of the medical instrument and configured for controlling and operating the medical instrument. The embodiment also includes a sound capability comprising a sound card within the computer or the sound capability forming a portion of the computer, a speaker for generating sounds from the sound capability, and a control panel for selecting the sounds, wherein the medical instrument generates a plurality of undesirable noises and wherein the computer, the control panel, the sound capability and the speaker are configured for processing digital files and to generate music or sounds to mask the noises or to mask perception of the noises, and optionally to allow a user or operator of the medical instrument to select the music or sounds.

Another embodiment is a medical instrument. The medical instrument includes a medical instrument for patient care, laboratory use, or pharmaceutical use, and also includes a computer, the computer forming a part of the medical instrument. The medical instrument also includes a sound card connected within the computer or a sound capability forming part of the computer, a speaker for generating sounds from the sound card, and a control panel for selecting sounds and adjusting a volume of the speaker, wherein the computer, the control panel, and the sound card or sound capability are configured for generating a plurality of sounds from a digital file and are configured to optionally allow a user or operator of the medical instrument to select the sounds to mask noises from the medical instrument.

Another embodiment is a medical instrument, the medical instrument selected from the group consisting of a blood separation machine, a peritoneal dialysis machine, a hemodialysis machine, an automated drug preparation machine, an automated sample preparation machine, and a machine for pumping or mixing medical fluids. The medical instrument also includes a computer, the computer forming a part of the medical instrument and configured for operating and controlling the medical instrument, a sound card operably connected to the computer or a sound capability forming part of the computer, a speaker for generating sounds from the sound card or sound capability, a control panel for selecting sounds and adjusting a volume of the speaker, wherein the sound card or sound capability is configured for generating a plurality of sounds from a digital file and wherein the computer, control panel, sound card or sound capability, and the speaker are configured for optionally allowing a user or operator of the medical instrument to select and generate sounds from the digital file to mask noises from the medical instrument.

Another embodiment is a method for masking noises from a medical instrument. The method includes selecting a medical instrument that makes undesirable noises, operating and controlling the medical instrument with a computer having an internal sound capability and a speaker, selecting at least one digital file for masking the undesirable noises, the medical instrument optionally programmed for making a default selection, and playing the sound using the internal sound capability and the speaker, wherein noises from the medical instrument are at least partially masked by sounds from the internal sound capability and the speaker.

Additional features and advantages are described herein, and will be apparent from, the following Detailed Description and the figures.

DETAILED DESCRIPTION

Embodiments of the present invention may form part of a medical instrument. Any device that generates undesirable noise will receive the most attention when it is used or operated over a period of time in close proximity to an operator or user of the device. Thus, if a noisy testing machine or compressor can be located far away in a sound-proof room, it will not generate its noise near people and thus will not draw complaints. Many machines, including medical instruments, must operate in close proximity to one or more people for one reason or another. If these machines or instruments are used in close proximity for a longer period of time, perhaps hours, the person or persons in close proximity will see the need for a measure of noise control.

There are many ways to conceal or disguise the noise coming from such a machine. Of course, a first option is to do nothing to reduce the noise from the machine. The users or operators may be left to fend for themselves, and could presumably use self-help techniques, such as ear-plugs, or perhaps a personal device, such as a portable radio, CD, or MP3 or other player, preferably with ear buds or headphones. A minimal step to assist in patient comfort would be to add muffling or baffles within the machine to reduce the overall level or noise. Another step would be to add noise, e.g., a pleasing sound that would drown out annoying noise made by an mechanical component. Another example would be to run continuously a noise that otherwise would cycle on and off, perhaps in an unpleasant or screeching manner. Of course, one could do both of these latter steps, i.e., an overall noise reduction or baffling effort combined with certain added noises to make the overall experience more pleasing to the patient. The inventors have now added another option, adding a level of digitally-generated noise to reduce perception of at least some of more objectionable noises emanating from the medical instrument. This may also be combined with a reduction in the amount of noise generated by the instrument.

A consumer preference test was conducted among 17 dialysis patients and 57 employees of the assignee of the present patent to see which method would be preferred. The test was thus conducted among 74 panelists divided into two panels. The first panel tests were conducted in Waukegan, Ill., in October, 2006, and a second panel in Pinellas Park, Fla., also in October, 2006. Panelists were asked to listen to various types of machine noises, consisting of existing and prototype instruments, as well as digitally modified sounds. Various sample noises were presented that employed noise reduction techniques as discussed above. The data obtained from the panelists ranked the sounds in order of preference.

Figure 1:
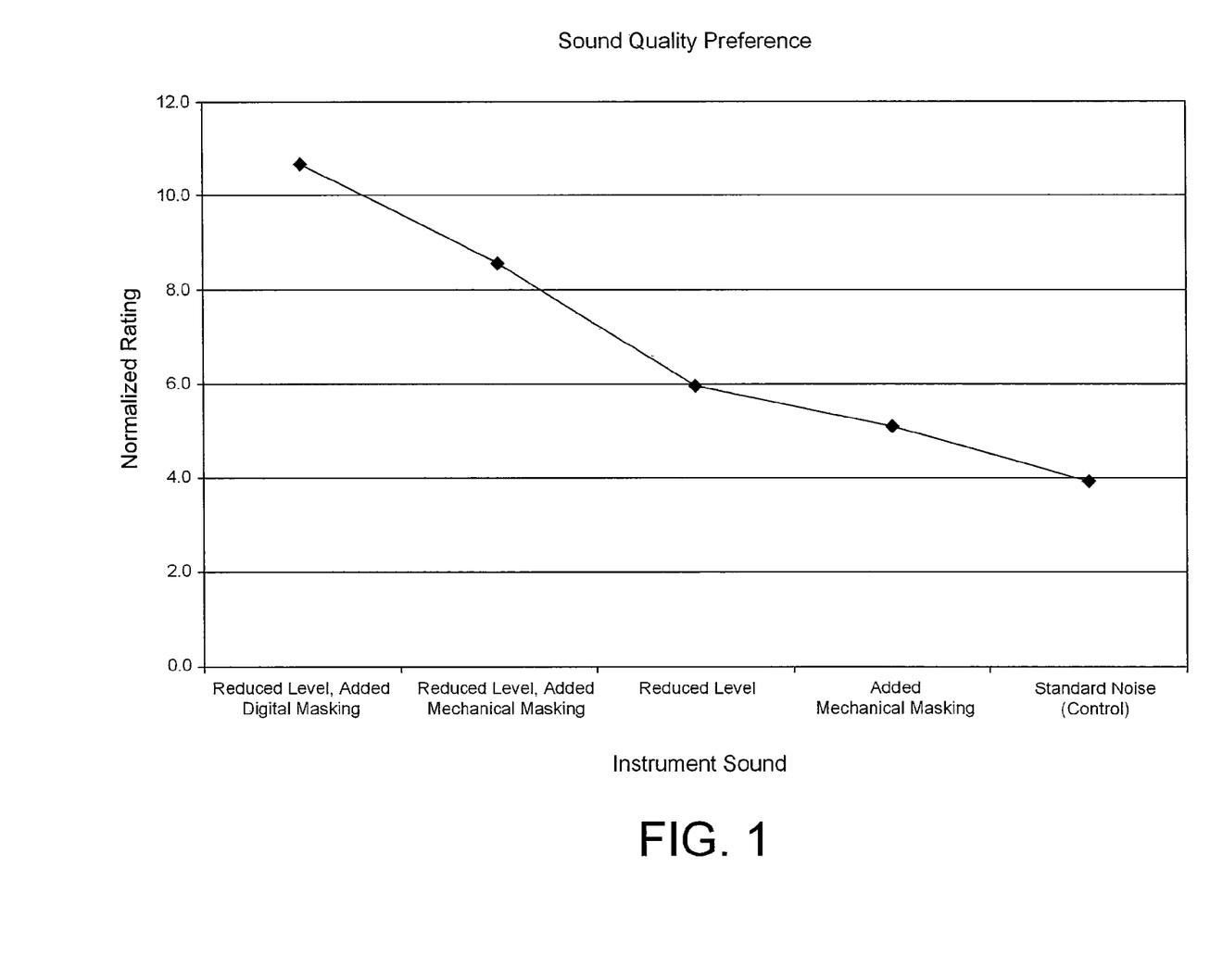
FIG. 1 is a chart depicting one test of consumer preferences for methods of masking noise.

The normalized results of the survey are depicted in FIG. 1. Reduced noise levels were strongly preferred, with either mechanical masking or digital noise added. Most preferred was an overall reduction in machine noise combined with digital noise masking. The digital sounds that were added included "white noise," as well as the extracted mechanical masking noises from actual instruments. The perceptions and preferences of the panelists were consistent with each other, with no significant difference in the rankings of the sounds between the employee and patient groups. Based on these tests, the inventors concluded that people who use dialysis machines would appreciate an improved medical instrument with masking sounds to reduce the perception of noise generated by the dialysis machine. The inventors also concluded that this concept could be extended to other medical instruments and devices with high noise levels and close contact with the people who operate them or use them.

Figure 2:
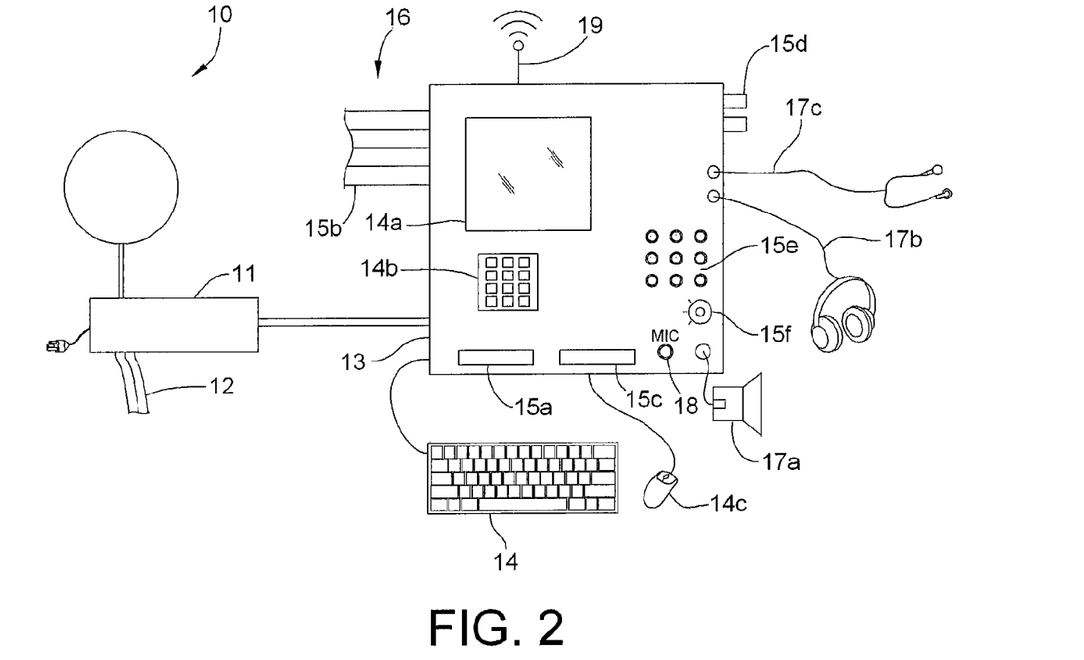
FIG. 2 is a schematic diagram of a first embodiment of a medical instrument that generates masking sounds.

An example of such an instrument is disclosed in FIG. 2. Medical instrument 10 may be any medical instrument that generates undesirable noise. If the medical instrument is a dialysis device, such as a peritoneal or hemodialysis device, it may generate noise such as the hum from the constant pumping or compressing of air. A sporadic clicking noise may be generated by opening and closing pneumatic valves. A hissing noise may be generated from the inflow of air to the pump or compressor, and a rush may be generated from the exhaust of air from the instrument.

Medical instrument 10 includes an operating portion 11, including fluid lines 12 for connection to a patient. An operating section 11 may perform a dialysis or other function for the patient under the supervision of a control section or computer 13. Computer 13 will preferably have at least an input keypad 14, control panel 14a, which may be a touch screen, input number pad 14b, and mouse 14c. The computer will also include input drive 15a, which may be suitable for a floppy drive or for a CD drive. The computer will preferably be configured with a port for Internet access 15b, as well as additional inputs and outputs, including ports 16. The additional input ports may be any combination of serial ports, such as USB ports, or parallel ports. In some embodiments, the computer will be adapted to receive commands from a remote control unit, and will include an IR receiver 15c for a hand-held remote. Inputs/outputs may include an optical input or output 15d and other digital or analog inputs. Control portion 15e includes a series of controls knobs or switches for adjusting sound level output by frequency. There is preferably an overall volume control 15f. In order to mask noises made by the medical instrument, the instrument now includes at least one speaker 17a (or headphones 17b or earbuds 17c) and preferably also includes a microphone 18, and an antenna 19 for receiving at least remote commands or information. The antenna may be used for wireless (WiFi) internet access or may be used for remote, but closer, commands.

In operation, the medical instrument, such as a dialysis instrument, is connected to a patient for a procedure, such as a dialysis treatment. When the machine is activated, the annoying sounds begin. The machine may automatically begin to play music or a masking noise, or an operator or user may enter a command to activate the music or masking noise. The command will be entered through the keypad, a keyboard, the control panel of the computer, or from a remote control unit. The computer will begin to play a digital sound or music file that has been entered into the computer. The music may be any music that is pleasing to the patient or to the clinic or hospital operating the medical instrument. If a masking sound is preferred, white noise or pink noise (less high frequency content) may be used. Other types of shaped random noise may be specifically engineered to effectively mask particular instrument sounds, and would be included as appropriate for that device. Other sounds may include soothing environmental sounds, such as water sounds, wind sounds or others. Such sounds typically have a theme, even a repetitive theme, but with sufficient variation that the sounds are both interesting and soothing. A variety of recordings of such sounds, including air conditioner hums, air purifier noise, fan or dryer noise, rainfall, running water, babbling brook, ocean wave sounds, and so forth, are available from PureWhiteNoise.com, Tallahassee, Fla., USA.

The computer will preferably have a sufficient variety of music or sound files to last for at least as long as the period of treatment. It should allow for looping of sounds or music playlists, or for setting a specific sequence of sounds for the course of the therapy. The computer should also have sufficient variety so that the same recording(s) are not repeated every time the patient returns for treatment. Besides environmental sounds, music may also be used. Music is available from a variety of sources, and a patient may even have his or her own copies of preferred music, so the ability to upload new content to the instrument is desired.

In addition to one or more speakers, which may be integral with the computer or the medical instrument, or may be separate, it is preferable, but not necessary, to use a microphone in embodiments described herein. The microphone may be used to detect sound levels and frequencies resulting from operation of the medical instrument and from playing the masking noise or music. The user or operator of the medical instrument may prefer to adjust the volume of the masking sounds simply by ear. Alternately, the user may program the computer to adjust the sound level based on the noises made by the medical instrument.

If the computer is programmed to adjust sound levels based on the noise generated by the medical portion of the instrument, the programmer should be careful to avoid any "siren" effect. A siren effect is a monotonous rise and fall of frequency, and typically volume, mimicking the noise made by an ambulance or police car. This is not a soothing sound, and may be avoided by selecting a constant noise or by damping variations in the sound. For instance, a program for moderating the masking noise may use a threshold volume of 50% or 75% of the maximum volume of the annoying noises, and may also use a faster reaction for increasing volume than for lowering volume. That is, the masking sounds or music may vary, but will not lower the volume sufficiently so that the annoying sounds are heard. In addition to "siren" effect changes in frequency, other transient noises that arise during the operation of the instrument may need to be obscured or masked. Masking sounds may be pre-programmed to change as needed prior to, or coincident with, such transients. Control algorithms may additionally respond in real time to detect deviations in noise.

Medical Instruments

Figure 3:
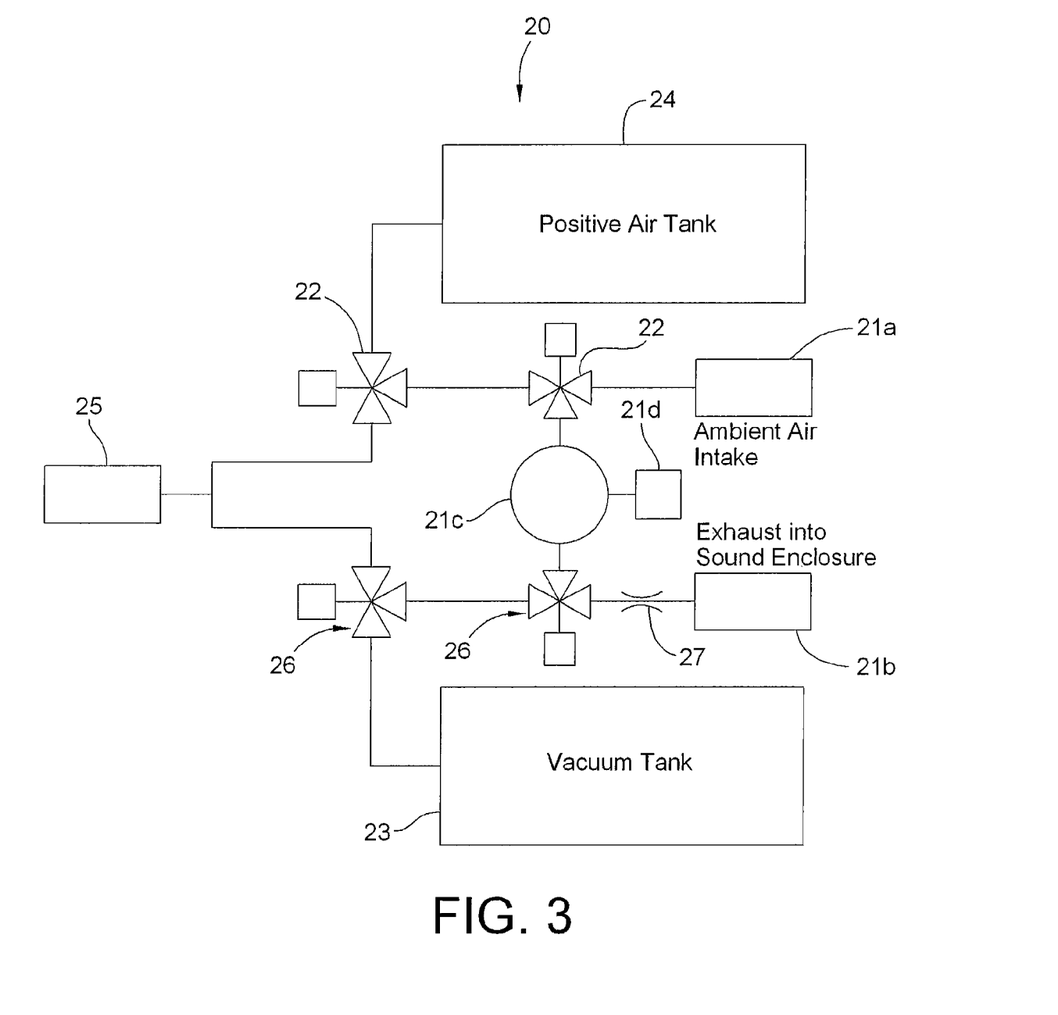
FIG. 3 is a schematic diagram of a portion of a medical instrument that generates undesirable noise.

The medical instrument which requires masking noises or sounds may be any of a great variety of medical instruments or machines. One example of a pneumatic portion of a renal care machine that requires masking is depicted in FIG. 3. Peritoneal dialysis (PD) machine 20 typically includes a compressor or pump 21c for compressing air to operate the dialysis machine 25. The pump may also be used to pump air from a tank 23, creating a partial vacuum. Noises include those made by the pump 21c, its motor 21d, and noises from each valve in the system, as well as the rush of incoming air from an ambient air intake 21a, which may be muffled, and the exhaust of air, preferably into a sound enclosure 21b. The noise from the pump generally depends on the pressure differential being generated by the pump, and can be very noisy at a high pressure differential, such as 7 psid. Of course, the noise level also depends on the flow rate of the air, with higher flow rates generating higher noise levels. Enclosures help to suppress the sounds of the air flows and the compressor or pump noises, much as a muffler helps to minimize the noise of a car engine. These measures are effective, but by analogy, when a person must sit beside a quiet machine for hours, even these muffled noises will become annoying.

Other noises will include clicks or bangs as three-way inlet valves 22 open or close to admit compressed air into the positive pressure air tank 24 or to admit small amounts of pressurized air into the PD machine 25. Noises will also be generated by operating valves 26 to admit air to or from vacuum tank 23 or to exhaust the air, preferably into a sound enclosure 21b. A baffle or orifice 27 in the exhaust line will create a back pressure when three-way outlet valve(s) 26 open to exhaust air from the PD machine. This will minimize the noise of the air rushing through the lines, with minimal effect on the timing of the internal workings of the PD machine. Restrictive baffles or orifices may be placed at other points in the air path to create a back pressure, enabling the system to pump at a constant, if higher, pressure and generate less noise. As noted, this can be minimized by exhausting into a muffled enclosure 21b. In addition to in-line muffling technologies, enclosing subsystems in sound reducing enclosure can help to reduce noise levels.

The task of masking noises from the machine described above is made difficult because the machine itself, like most medical machines or instruments, is already highly-engineered. The components and subsystems of the machine have typically been made as quiet as possible, and steps taken to reduce noise at their source. Sound absorbing and reflecting materials are used in conjunction with enclosures and baffles, as discussed above, to trap and dissipate sound energy. The machine may even use control schemes and algorithms to reduce noticeable and offensive transient noises, with special attention paid to the intake and exhaust systems. Manufacturers are aware of the need to enhance the quality of life for the patients using their machines. Obvious steps, such as minimizing air noise, will likely have already been taken. The air pressure differentials may be low, e.g., about 4-5 psi (about 40-50 kPa) above atmospheric for the positive pressure air tank, and about 4-5 psi (about 40-50 kPa) below atmospheric for the "vacuum" tank. Thus, when air is compressed, stored, used and exhausted, the quantities and pressures are minimal, even when compared to pressures used to inflate a tire (30-35 psig, about 205-240 kPa).

At the pressures used in the medical instrument, the obvious noises are likely already minimized, and further improvements in one area, e.g., quieting the pump, may simply make other noises more obvious, e.g., the rush of the air or the clicking of the valves. As pointed out, masking the noises, rather than further noise reduction, may be the more desirable option.

A variety of other medical instruments may benefit from the use of masking noises or music. For example, blood separation machines are used to separate red blood cells from whole blood of volunteers. The donated red blood cells are then used to treat victims of trauma, persons with certain types of cancer, or persons with sickle cell anemia. An example is the Alyx centrifugal blood separation machine made by Fenwal, Inc., of Round Lake, Ill., USA. This machine includes pumps, clamps and valves that move the volunteer's blood through the machine. Blood separators are typically found in municipal or regional blood centers. Even though a patient is typically connected to the machine for less than one-half hour, the blood separator would benefit from soothing music or distracting white noise to mask the sound of the centrifugal whirring, the clicking of the valves, and the hiccupping sound of the clamps opening and closing. The beneficial effects would also be noticed by the nurses supervising the volunteers, who are in contact all day with the separator.

There are many other examples. For instance, many laboratories or preparation facilities use centrifugal machines or mixers for to prepare samples for analysis. Other machines are used to prepare doses of a medicine for immediate consumption. Such machines are made by PerkinElmer Life and Analytical Systems, Inc., Shelton, Conn., USA and Parata Systems, Inc., of Durham, N.C., USA, among others. While not meaning to specifically point out these manufacturers or their machines, they may be typical of medical instruments or devices that generate noise. They may benefit, among many others, from a noise masking system that is used with and controlled by the machine itself.

Hardware to Generate Music or Masking Sounds

Figure 4:
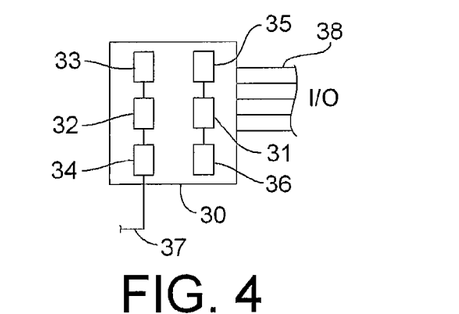
FIG. 4 is a schematic diagram of a sound card useful in embodiments.
Figure 5:
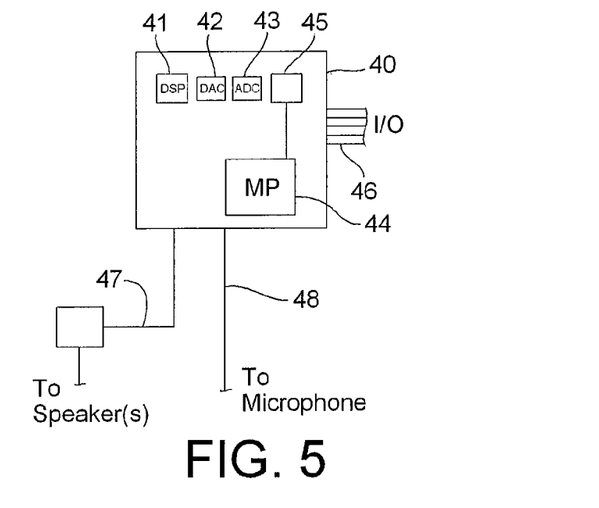
FIG. 5 is a schematic diagram of a motherboard with a built-in sound capability useful in embodiments.
Figure 6:
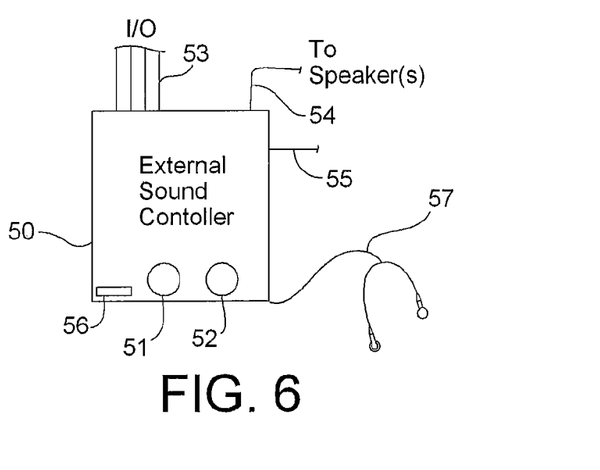
FIG. 6 is a schematic diagram of an external sound controller that may be used in embodiments.

The hardware used to play the masking sounds or music may include any of the devices depicted in FIGS. 4-6. The options for the computer typically include, but are not limited to, a sound card, a sound capability built into the computer motherboard, or an external sound control. These are options that may be used, but any other suitable hardware may be used instead or in addition to these. As shown in FIG. 4, a sound card 30 is typically mounted on a printed circuit board (PCB) and includes digital signal processor (DSP) 31 and a memory 32, along with its own microprocessor computer 33, a digital to analog converter (DAC) 34, an analog to digital converter (ADC) 35, and a PCI (peripheral component) interface 35 to the instrument computer. Some embodiments use a coder/decoder (codec) chip 36 to perform the functions of the ADC and DAC converters. The sound card also includes numerous input/output lines 38, at least for connection to the instrument computer and one or more speakers, such as output 37. It is possible that the user may desire to send the output to a separate player, such as a digital audio player, also known as a DAT player. It is desirable to include an input connection for a microphone or an output connection for headphones. Sound cards are available from many manufacturers and typically have excellent performance. If a medical instrument or device can accept and utilize a sound card, this would be a preferred way to adapt the instrument.

Rather than adding a separate sound card, a computer may be equipped with an integral sound capability residing it its motherboard or other circuitry, as shown in FIG. 5. Circuit board 40 may include a central microprocessor controller computer 44, and numerous other hardware for storing and reading digital files and generating music or sound. These include a digital signal processor 41, a digital to analog converter 42, an analog to digital converter 43, a memory chip 45, and optionally, a codec chip (not shown). The board will have numerous input/output lines 46, preferably including separate outputs 47 for one or more speakers and an inlet line 48 for a microphone. In order to use this option, the medical instrument or device would likely be designed from the start to include the sound capability. Alternatively, the system might require extensive modification to add such a sound capability.

Another hardware option is to add an external sound capability to the computer that operates the medical instrument. An external sound control includes all the components discussed above that are necessary to read a digital file and play music or sound from the file. External sound controls, such as "Sound Blaster," are available from Creative Labs of Milpitas, Calif., USA. External sound controls are also available from Griffin Technology, Nashville, Tenn., USA. As shown in FIG. 6, the external sound controller 50 may include controls 51, 52, such as for volume and frequency mix (bass/treble). The sound controller includes numerous input/output lines 53, and preferably includes separate lines 54 for output speakers 54 and for a microphone 55. External sound controls may also include a remote capability, using a remote window 56. An audio output 57 for headphones or earbuds may also be used.

It is possible to use other players to input digital files, such as a mini-disc player using an optical medium (e.g. a Sony MD Walkman) or an MP3 player (such as an MP3 Walkman or an Apple iPod), or other devices, such as standard CD players. It is also possible to output converted files to a separate player, such as an optical output to a mini-disc player or a DAT player, rather than to the usual speaker(s) or headphones. Not shown are the internal components, which are typically similar to those used for sound cards and an integral sound capability, such as a microprocessor, a digital signal processor, memory, an ADC, a DAC, and so forth. If an existing medical instrument or device cannot accommodate a sound card, it may be simpler to connect an external sound capability.

Methods for Using Masking Sounds and Music

Embodiments may use the hardware described above, and the medical instrument or device may also include programming to insure satisfactory performance. It has been found that the frequency distribution of noise, such as white noise, can have a profound effect on the sound pressure levels necessary to achieve masking that is not unduly annoying. One example is U.S. Pat. Appl. Publ. 2003/0144847, published on Jul. 31, 2003, and which is incorporated herein by reference in its entirety, as though each word and drawing were appended hereto. This publication teaches the effectiveness of masking noise with a frequency having a substantially constant negative slope over the frequency range of the human voice, from about 200 Hz to about 5000 Hz. The slope is desirably about −4 db per octave, and may be between about −2 to −6 db per octave. With this distribution, the overall dB level of masking sounds needed to mask at least voices is significantly reduced. More generally, masking sounds should have a spectrum that is a close match to the spectrum of noise that is to be masked. Embodiments of the present invention, however, are not limited to these ranges.

Accordingly, when the frequency and sound pressure (noise) levels of a medical instrument are documented, the masking noise or music may be tailored so that the sound pressure level or decibel level of the music or noise may be used to just exceed the dB level of the medical instrument. The tailoring or variation in the masking noise, however, should not be so abrupt that it rises to the level of a "siren" effect, which is typically much more annoying than normal instrument or machine noises. Of course, masking sounds should be used primarily in the range of human hearing capability, from about 20 Hz to about 20 kHz (20,000 Hz). A table of the octaves used in studying hearing is listed in Table 1.

TABLE 1

| Octave Band | Frequency Range, Hz | Central Frequency |
| --- | --- | --- |
| 1 | 20-40 | 30 |
| 2 | 40-80 | 60 |
| 3 | 80-160 | 120 |
| 4 | 160-320 | 240 |
| 5 | 320-640 | 480 |
| 6 | 640-1280 | 960 |
| 7 | 1280-2560 | 1920 |
| 8 | 2560-5120 | 3840 |
| 9 | 5120-10,240 | 7680 |
| 10 | 10,240-20,480 | 15,360 |

Source: EURASIP Journal on Applied Signal Processing 2005: 18 3015-3025, "A Low Power Two-Digit Multi-Dimensional Logarithmic Number System Filterbank Architecture for a Digital Hearing Aid," by Roberto Muscedere, Vassil Dimitrov, Graham Jullien and William Miller, Research Center for Integrated Microsystems (RCIM), University of Windsor, ON, Canada.

Figure 7:
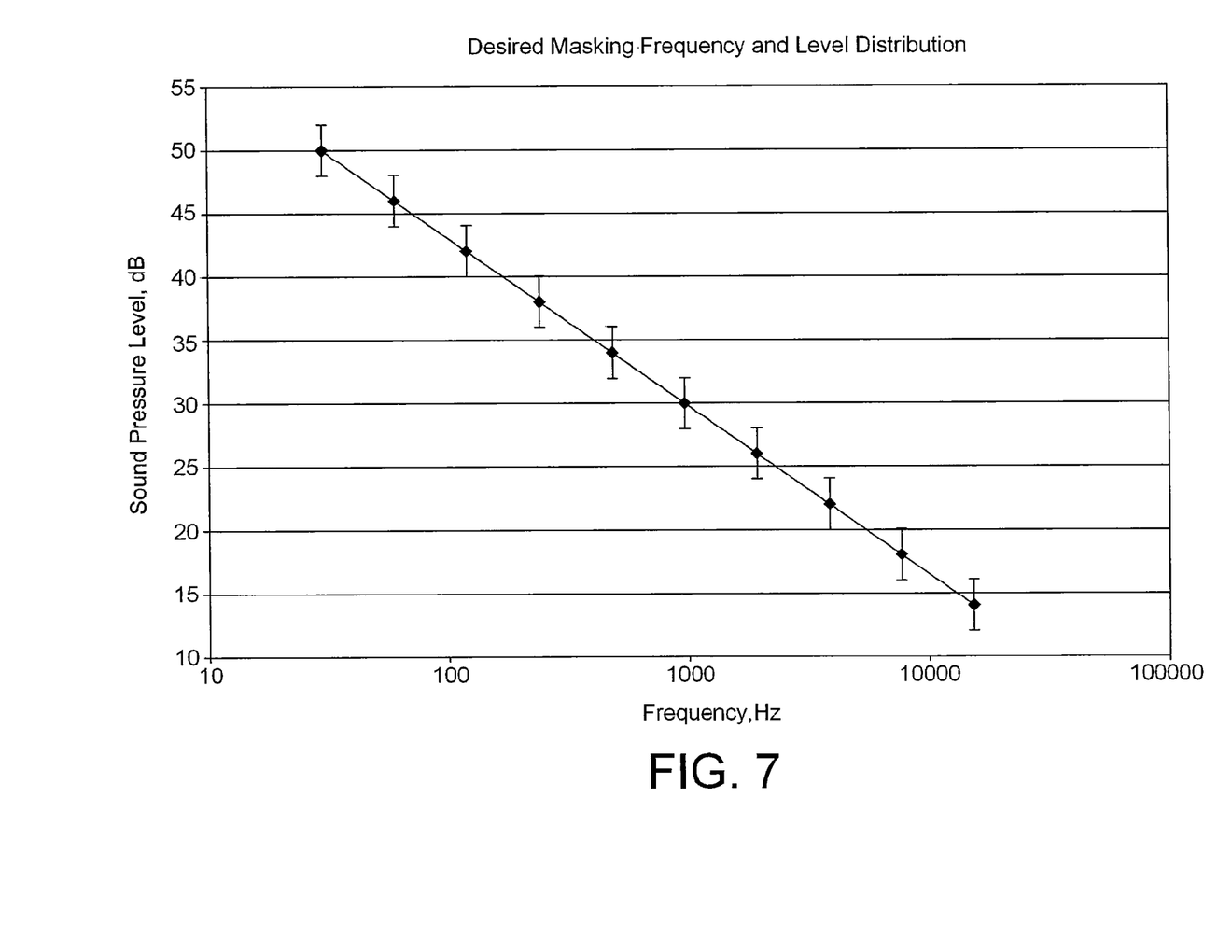
FIGS. 7-8 are graphs of desired distributions of sound pressure (noise) levels at frequencies of human hearing.
Figure 8:
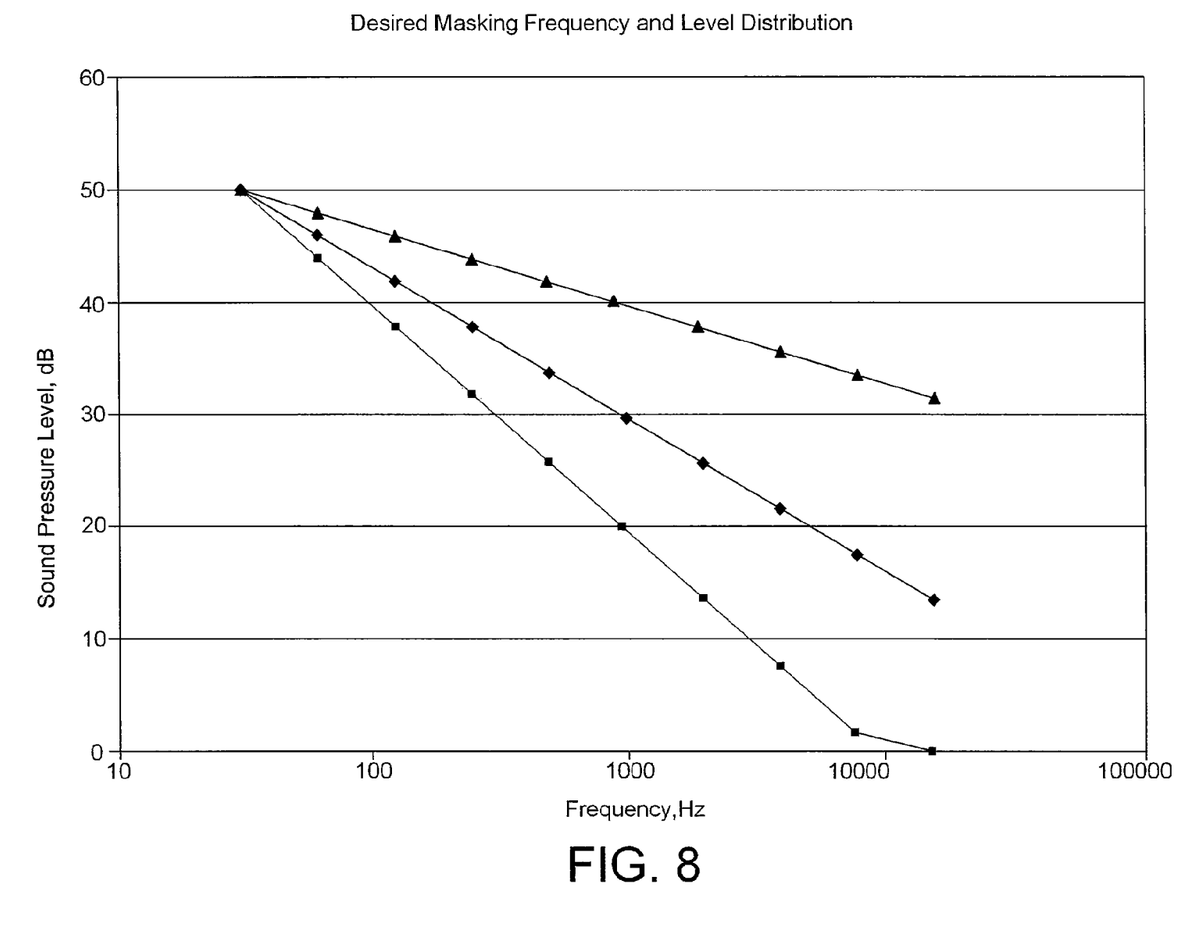

The masking noise will desirably have a frequency distribution with a substantially constant negative slope from about −2 to about −6 dB per octave, preferably about −4 dB per octave, as noted. An example is depicted in FIG. 7, with a slope of −4 dB per octave. Error bars on the vertical axis are set for ±2 dB, to demonstrate the preferred range of slope. Low frequency machine noises, especially those at the 60 Hz and its harmonics, 120 Hz, 180 Hz, and so forth, will be very noticeable to persons close by. However, if they are distracted by noise at higher frequencies, but not at higher sound pressure levels (dBs), the absolute level of the noise needed to mask the medical instrument may be lower than otherwise expected. Typical noise criteria curves will drop off more steeply at lower frequencies, generating less sound at low frequencies, and will drop off less steeply at higher frequencies, generating more sound than may be necessary. It appears that it is more important that the slope of the distribution is constant, rather than the precise value of the slope, within these limits. This will help to minimize the total level of sounds needed to mask the noise of the medical machine. FIG. 8 depicts frequency and noise levels at constant slopes of −2, −4 and −6 dB, with −2 dB being the flattest curve while −6 dB has most dramatic sound level drop-off.

Audio playback equipment may include a graphic analyzer or equalizer, or less frequently, a parametric equalizer. This equipment may be used in accordance with the principles discussed above to tailor the playback for greater filtering or cut-off at progressively higher frequency bands. Some equipment uses only 5 frequency bands for the entire audio range, while others use at least octaves, and will have 9 or 10 bands, each of which may be assigned a dB value for amplification or attenuation. As discussed, a substantially constant slope of −4 dB octave is preferred. Some equipment may have bands for each ½ octave, so that 18 to 20 bands (and settings) are possible, while the best equipment has bands for each ⅓ octave, with 30 or 31 bands and settings possible.

A particular digital file may be analyzed and settings on a graphic equalizer, or preferably a parametric equalizer, may be optimized for maximum masking effect. The settings may be chosen on the basis of consumer preference, analysis of feedback from executing the file, or simply entering settings corresponding to a desired slope of amplitude or volume versus frequency. It should be noted that this procedure amounts primarily to shaping and filtering a particular signal, and does not affect the signal file (recording) itself. For instance, if the digital file has very low volume or amplitude at low frequencies (bass), 5 to 10 decibels of amplification at that frequency may not be sufficient to achieve the desired optimal output sound level at that frequency, and it may be necessary to boost the amplification at that or surrounding frequencies. In a similar manner, if the high frequencies (treble) have very high volume or sound level, a few decibels of attenuation may not be sufficient to lower the sound level to match that area of the preferred slope. Particular recordings or digital files may require different adjustments. Ultimately, user or operator perception of masking should decide the particular settings and output volume of the masking equipment.

Figure 9:
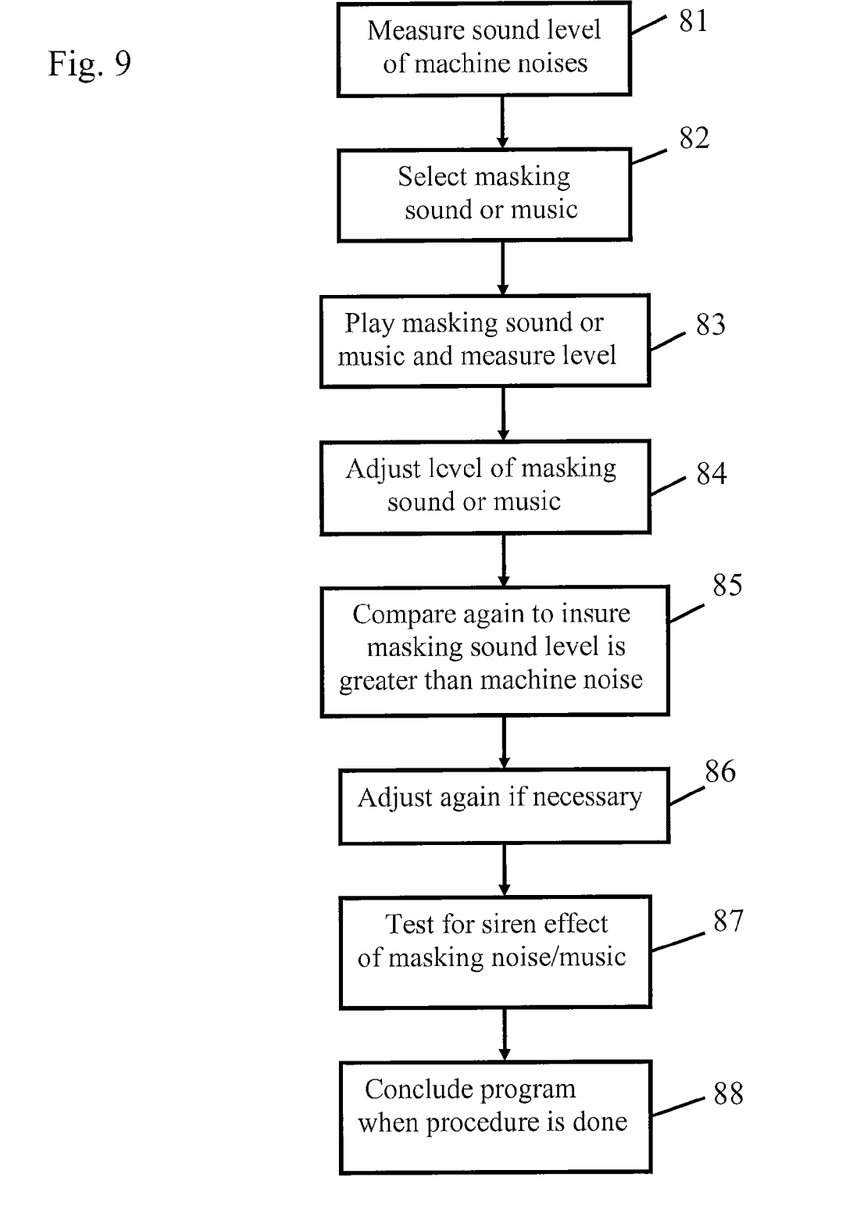
FIGS. 9-10 are flowcharts for methods of using masking sounds or music to provide a more comfortable environment for patients or users.
Figure 10:
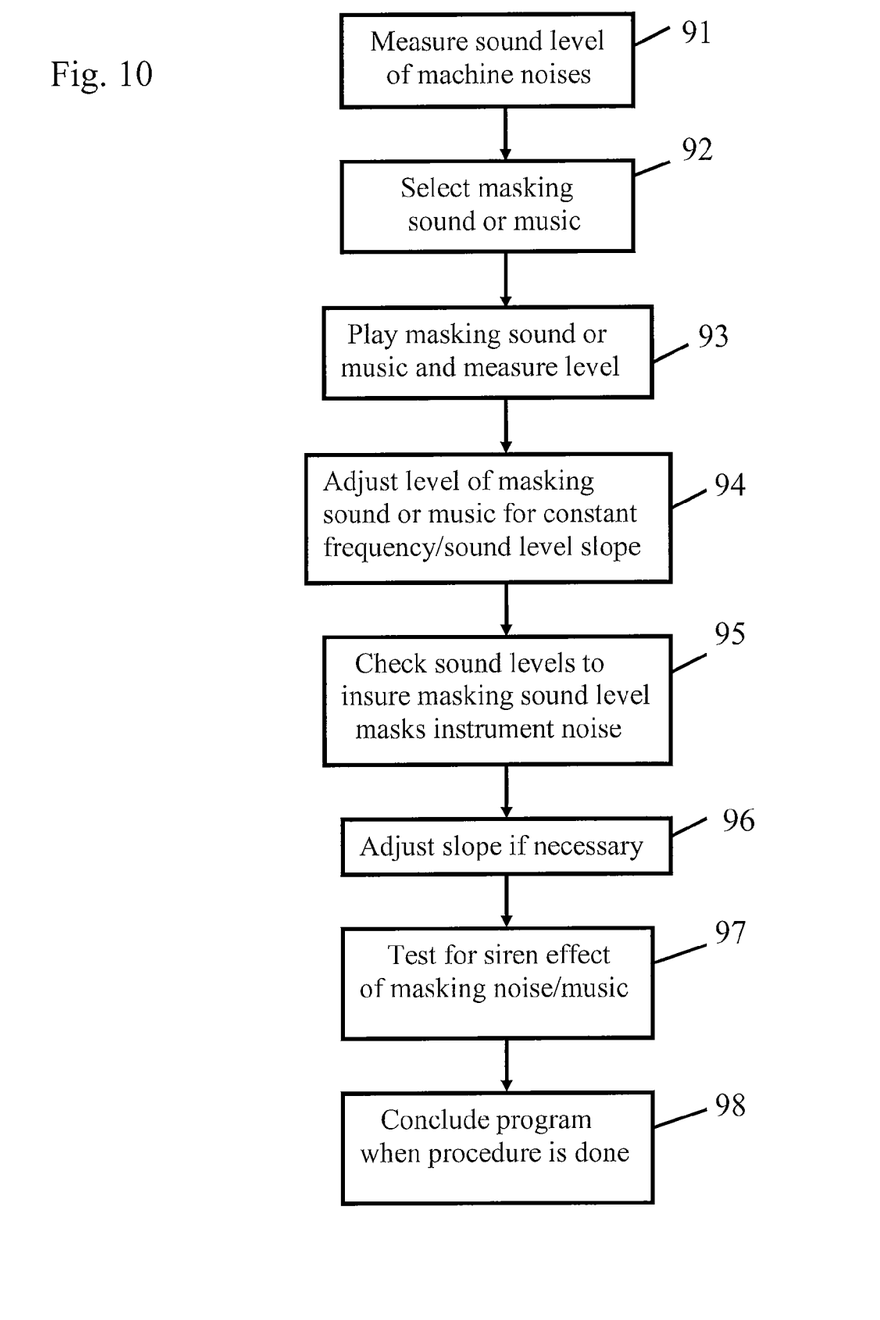

Embodiments include methods of using sounds and music to mask the noises made by medical instruments and machines. Two methods of the many methods possible are depicted in FIGS. 9-10. A first step 81 is to measure absolute noise levels of the instruments in question. This step may be avoided and a measure of the output sound taken "by ear" for comparison, but overall noise and music levels may be minimized by careful attention to feedback from such details. It is clearly desirable, but not absolutely necessary, to obtain an analysis of the frequency and sound pressure level distribution of the instrument before beginning. A masking sound or music selection may then optionally be made 82. A test run may then be made, playing 83 the sound or music, and measuring the level of sound or music against the instrument or machine noise, preferably in several portions of the frequency spectrum. The test may be run with sound-measuring instruments, or may be run with a test panel of persons.

After the first test is run, and using feedback from the first test, the level of masking sound or music may be adjusted 84 and again compared 85 with instrument noise for absolute noise level comparison or for comparison by human perception. The sound or music may then be adjusted if necessary 86. The testing should include a check 87 that the generated masking sounds do not yield a siren effect, or other objectionable effects or sounds from a sound-quality perspective. For example, checks on sound roughness, amplitude modulation, and so forth, may also be used to ensure that sounds generated are pleasing and soothing to the patients or users of the devices. The program for generating masking sounds of music may be concluded 88 when the particular procedure is completed. Other methods of masking sounds may also be used.

In another embodiment, the equipment used to generate masking sounds may be programmed to keep the slope of the frequency/sound level distribution, as discussed above, to a substantially constant negative slope, preferably −4 dB per octave, but also possibly including slopes from −2 to −6 dB per octave. This embodiment uses a method similar to that discussed above for FIG. 9, but also paying attention to the slope. It is easier to follow this method when using generated noise, such as white noise or pink noise, or soothing environmental sounds as discussed above, rather than recorded music. The method of FIG. 10 includes using a substantially constant slope of a frequency/sound pressure level logarithmic graph. The first step 91 is to measure the sound level of noises generated by the medical instrument, over the appropriate frequency range. Appropriate masking sounds or music, preferably having a frequency profile with the potential to mask the machine noise, are then optionally selected 92.

The masking sound or music is then played and the sound levels over the frequency range are measured and compared 93 to the machine noise. The level of the masking noise or music is then adjusted 94 for a substantially constant slope of sound level versus frequency. The test may then be run again, checking the altered sound levels 95 at frequency to see if the machine noises are indeed masked. The comparison is preferably accomplished with both technical data and consumer perception. Any adjustments, such as the output for a particular frequency range, may then be made 96, with particular emphasis put on the constant slope of the curve. When this has been accomplished, a test may be run 97 to insure that any siren effect is not noticeable. The masking program may then be concluded 98 when the medical, laboratory, and clinical procedure has been accomplished.

Figure 11:
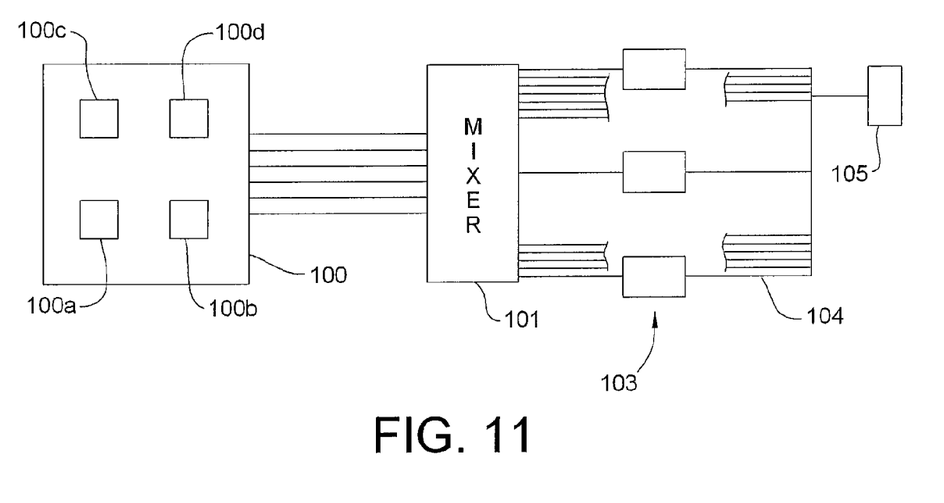
FIG. 11 depicts another embodiment of a signal processing for improving the masking of medical instruments.

The appropriate sound level distribution over frequencies may be achieved with an apparatus as described in FIG. 11. A signal processor 100 is preferably a sound card, with a DSP 100$a$, a DAC 100$b$, an ADC 100$c$ and memory 100$d$. A PCI interface (not shown) may also be desirable. The digital signals from a digital music or sound file are sent to a sound mixer 101, where the signals are segregated into octaves, of more preferably ½ octave bands, or even more preferably into ⅓ octave bands and then sent to a series of filters or "equalizers" 103. In one embodiment, there may be 10 "equalizers," or sound level adjusters, for the 10 octave bands. In other embodiments, there may be about numerous ½ octave bands or even more numerous ⅓ octave sound level adjusters, such as 28 to 31 bands and filters.

In this instance, the "equalizers" are not used merely to equalize the output sound levels, but rather to apply a bias to the frequency distribution, as discussed above. The equalizers are thus used as sound level output adjusters that adjust the slope of the sound level/frequency distribution. The slope should be substantially constant and should be from about −2 dB per octave to about −6 dB per octave. Other output slopes may also be used, however. The outputs of the filters are then combined into output 105. The outputs are preferably analog outputs to be sent to the speaker(s) of the masking system. The outputs could be digital outputs and could be sent to an amplifier, if necessary, if the noise levels require, before being played through a speaker, but this should not be necessary for a single medical instrument. Adjusting the dB levels of the filters or "equalizers" allows a user or operator to select the sounds output by the medical instrument.

The equalizers may also be used to specify changes in overall sound level, dB per frequency or frequency band, and adjustments to the nature or dimension of the sound with respect to parameters of sound perception. These dimensions may include sharpness, roughness, modulation, or any other desired measure of sound quality. In some embodiments, operators and users may select which particular sounds or music to play. In other embodiments, the medical instrument may be programmed in advance to play one or more tracks or recordings, or to mix tracks or recordings in a pre-set or random manner.

It is also possible to simultaneously use more than one sound track or digital file to generate masking sounds. The files may be mixed and played at selected volumes, perhaps a higher level of a white noise file and a lower level of a soothing environmental sound, such as ocean wave noises. Such techniques are well known and are described in U.S. Pat. Appl. Publ. 2003/0144847, discussed above. Other techniques may also be used. For instance, a music file or file that generates soothing sounds may be played and filtered or biased so that the output sound level decreases with frequency as discussed above. This recording may be done on-line and used, or may be created off-line and then stored in the medical instrument computer or memory for later use. Recordings with higher levels of sound output at frequencies at which the medical instrument generates noise may also be created and recorded for future use. Finally, the computer may be programmed to change recordings or files periodically, perhaps with gradual transitions, so that a variety of music or sounds is used, including silence or a turnoff after one or two hours. In some applications, such as overnight dialysis, the user may prefer to go to sleep with a little help from masking sounds or music. In other applications, such as a half-hour blood donation/separation, or a several hour day-time dialysis, a more lively and interesting variation in music may make the time pass more easily.

It should be understood that various changes and modifications to the embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical instrument, comprising:
a medical instrument for patient care, laboratory use, or pharmaceutical use;
a computer, the computer forming a part of the medical instrument and configured for controlling and operating the medical instrument;
a microphone operably connected to the computer and positioned and arranged to detect at least one of a sound level or a sound frequency residing outside of and resulting from an operation of the medical instrument;
a sound capability comprising a sound card within the computer or the sound capability forming a portion of the computer;
a speaker for generating sounds from the sound capability; and
a control panel for selecting the sounds,
wherein the computer, the control panel, the sound capability and the speaker are configured to (i) allow a user or operator of the medical instrument to select the sounds and to generate the selected sounds, (ii) adjust a frequency of the generated sounds, to mask the microphone-detected at least one sound level or sound frequency, so that at least one of (a) the frequency of the generated sounds increases as a sound level output of the generated sounds decreases or (b) the frequency of the generated sounds decreases as the sound level output of the generated sounds increases, and (iii) prevent the generated sounds from producing a siren effect due to a rise and fall of the sound level output or to the frequency of the generated sounds.

2. The medical instrument of claim 1, further comprising an input port configured for inputting a digital file.

3. The medical instrument of claim 1, further comprising an input configured for inputting a digital file, the input selected from the group consisting of an Internet connection, a USB port, a floppy drive, and a CD-drive.

4. The medical instrument of claim 3, wherein the digital file has a format selected from the group consisting of CD, CD-DA, CD-ROM, MP3, ITunes, WAV, WMA, AIFF, MPEG-4, AAC, a digital radio format, Vorbis and Speex.

5. The medical instrument of claim 1, wherein the microphone is positioned in an area outside the medical instrument.

6. The medical instrument of claim 1, further comprising a sound level control on the control panel.

7. The medical instrument of claim 1, further comprising a plurality of filters selectable by the user or operator for shaping the sounds.

8. The medical instrument of claim 3, wherein the digital file is a digital music file or a noise masking file selected from the group consisting of white noise, pink noise and soothing noise.

9. The medical instrument of claim 1, wherein a sound level of the generated sounds decreases at a slower rate than the microphone-detected sound level.

10. A medical instrument, comprising:
a medical instrument for patient care, laboratory use, or pharmaceutical use;
a computer, the computer forming a part of the medical instrument;
a microphone operably connected to the computer and positioned and arranged to detect at least one of a sound level or a sound frequency residing outside of and resulting from an operation of the medical instrument;
a sound card connected within the computer or a sound capability forming part of the computer;
a speaker for generating sounds from the sound card; and
a control panel for selecting sounds and adjusting a volume of the speaker,
wherein the computer, the control panel, and the sound card or sound capability are configured to (i) optionally allow a user or operator of the medical instrument to select the sounds to mask the microphone-detected at least one sound level or sound frequency, (ii) generate sounds or optionally the selected sounds from a digital file, (iii) adjust a frequency of the generated sounds, to mask the microphone-detected at least one sound level or sound frequency, so that at least one of (a) the frequency of the generated sounds increases as a sound level output of the generated sounds decreases or (b) the frequency of the generated sounds decreases as the sound level output of the generated sounds increases, and (iv) prevent the generated sounds from producing a siren effect due to a rise and fall of the sound level output or to the frequency of the generated sounds.

11. The medical instrument of claim 10, wherein the digital file is a music file and has a format selected from the group consisting of CD-DA, CD-ROM, MP3, ITunes, WAV, AIFF, MPEG-4, AAC, a digital radio format, Vorbis and Speex.

12. The medical instrument of claim 10, wherein the microphone is positioned near a patient and outside of the medical instrument.

13. The medical instrument of claim 10, further comprising a graphical analyzer configured for visually outputting information concerning at least the sound level output and optionally the frequency of the generated sounds.

14. The medical instrument of claim 10, wherein a sound level of the generated sounds decreases at a slower rate than the microphone-detected sound level.

15. A medical instrument, comprising:
a medical instrument, the medical instrument selected from the group consisting of a blood separation machine, a peritoneal dialysis machine, a hemodialysis machine, an automated drug preparation machine, an automated sample preparation machine, and a machine for pumping or mixing medical fluids;
a computer, the computer forming a part of the medical instrument and configured for operating and controlling the medical instrument;
a microphone operably connected to the computer and positioned and arranged to detect at least one of a sound level or a sound frequency residing outside of and resulting from operation of the medical instrument;
a sound card operably connected to the computer or a sound capability forming part of the computer;
a speaker for generating sounds from the sound card or sound capability; and
a control panel for selecting sounds and adjusting a volume of the speaker,
wherein the sound card or sound capability is configured to generate a plurality of sounds from a digital file, and
wherein the computer, control panel, sound card or sound capability, and the speaker are configured to (i) optionally allow a user or operator of the medical instrument to select and generate the sounds from the digital file, (ii) adjust a frequency of the generated sounds, to mask the microphone-detected at least one sound level or sound frequency, so that at least one of (a) the frequency of the generated sounds increases as a sound level output of the generated sounds decreases or (b) the frequency of the generated sounds decreases as the sound level output of the generated sounds increases, and (iii) prevent the generated sounds from producing a siren effect due to a rise and fall of the sound level output or to the frequency of the generated sounds.

16. The medical instrument of claim 15, further comprising an input configured for inputting the digital file, the input selected from the group consisting of an Internet connection, a USB port, an optical input, a floppy drive, and a CD-drive.

17. The medical instrument of claim 15, wherein the microphone is configured for feedback from an area outside the medical instrument and a graphical analyzer is configured for visually outputting information concerning at least the sound level output and optionally the frequency of the generated sounds.

18. The medical instrument of claim 15, further comprising a graphic equalizer or parametric equalizer operably connected to the medical instrument and configured for allowing the user or operator to shape the sounds output by the speaker.

19. The medical instrument of claim 15, wherein a sound level of the generated sounds decreases at a slower rate than the microphone-detected sound level.

20. A method for masking undesirable noises made by a medical instrument, the method comprising:
operating and controlling the medical instrument with a computer having an internal sound capability and a speaker;
positioning a microphone so as to detect at least one of a sound level or a sound frequency made by and residing outside of the medical instrument;
enabling a user or operator of the medical instrument to select at least one digital file sound for masking the microphone-detected at least one sound level or sound frequency, the medical instrument optionally programmed for making a default sound selection;
playing the selected sound using the internal sound capability and the speaker, wherein the microphone-detected at least one sound level or sound frequency is at least partially masked by the selected sound from the internal sound capability and the speaker;
adjusting a frequency of the selected sound to mask the microphone-detected at least one sound level or sound frequency so that at least one of (i) the frequency of the selected sound increases as a sound level output of the selected sound decreases or (ii) the frequency of the selected sound decreases as the sound level output of the selected sound increases; and
preventing the selected sound from producing a siren effect due to a rise and fall of the sound level output or to the frequency of the selected sound.

21. The method of claim 20, wherein the sound capability resides on a sound card or a printed circuit board forming a part of the computer or connected to the computer.

22. The method of claim 20, wherein adjusting the frequency of the selected sound to mask the microphone-detected at least one sound level or sound frequency further includes adjusting the sound level output of the selected sound with respect to the frequency of the selected sound so that a slope of the sound level output versus frequency is substantially constant and is from about −2 dB per octave to about −6 dB per octave, and optionally about −4 dB per octave.

23. The method of claim 20, wherein adjusting the frequency of the selected sound to mask the microphone-detected at least one sound level or sound frequency further includes adjusting the sound level output of the selected sound with respect to the frequency of the selected sound so that a slope of the sound level output versus frequency is substantially constant and is from about −2 dB per octave to about −6 dB per octave, and optionally about −4 dB per octave, and further comprising recording the digital file with an adjusted sound level output for further use in masking noises.

24. The method of claim 20, further comprising programming the medical instrument to play a variety of selected sounds over a period of time.

25. The method of claim 20, which includes using the microphone for feedback and automatically or manually adjusting an output level of the speaker in response to the feedback.

26. The method of claim 20, further comprising selecting a sound for masking or minimizing an impact of a particular noise from the medical instrument.

27. The method of claim 20, wherein two or more digital files are played simultaneously to generate masking sounds.

28. The method of claim 20, wherein a sound level of the selected sound decreases at a slower rate than the microphone-detected sound level.

* * * * *